United States Patent [19]

Johnson et al.

[11] Patent Number: 4,618,600
[45] Date of Patent: Oct. 21, 1986

[54] NOVEL POLYPEPTIDE DIURETIC/VASODILATORS

[75] Inventors: Lorin K. Johnson, Castro Valley, Calif.; Steven A. Atlas; John H. Laragh, both of New York, N.Y.

[73] Assignee: Biotechnology Research Associates, J.V., Mountain View, Calif.

[21] Appl. No.: 602,117

[22] Filed: Apr. 19, 1984

[51] Int. Cl.[4] ............... A61K 37/02; A61K 39/00; C07K 7/10
[52] U.S. Cl. .................................. 514/12; 514/13; 530/324; 530/325; 424/85
[58] Field of Search ............ 424/177, 85; 260/112 R, 260/112.5 R; 514/12, 13

[56] References Cited

U.S. PATENT DOCUMENTS

| | | | |
|---|---|---|---|
| 4,016,258 | 4/1977 | Said et al. | 424/177 |
| 4,113,711 | 9/1978 | Said et al. | 260/112 R |
| 4,237,046 | 12/1980 | Bodansky | 260/112.5 R |
| 4,496,544 | 1/1985 | Needleman | 514/13 |
| 4,508,712 | 4/1985 | Needleman | 514/11 |

FOREIGN PATENT DOCUMENTS 0116784 12/1983 European Pat. Off. .

OTHER PUBLICATIONS

Trippodo, et al., Proc. Soc. Exp. Biol. Med., 170, 502–508 (1982).
Debold, et al., Fed. Proc., 42(3), Abstract 1870, 611, Mar. 1, 1983.
Needleman et al., Fed. Proc., 42(3), Abstr. 1872, p. 612, Mar. 1, 1983.
Deth, et al., Fed. Proc., 41, (4) 983, Abstr. 4170, Mar. 5, 1982.
Debold, et al., Life Sci. 28, 89–94, at p. 94 (1982).
Debold, et al., J. Histochem. Cytochem., 26, 1094–1102 (1978).
Chem. Abstr., vol. 101, (1984) 33109z, 1565d.
Chem. Abstr., vol. 100, (1984) 115136z.
Chem. Abstr., vol. 99, (1983) 50843s.
Life Sciences, vol. 28, pp. 89–94, "A Rapid and Potent Natriuretic Response to Intravenous Injection of Atrial Myocardial Extract in Rats", by A. J. de Bold, et al., 1981.
Science, vol. 221, pp. 71–73, "Bioactive Cardiac Substances: Potent Vasorelaxant Activity in Mammalian Atria", by Mark G. Currie, et al., Jul. 1983.
Biochem. and Biophys. Res. Commun., vol. 117, No. 3, 1983, "The Amino Acid Sequence of an Atrial Peptide with Potent Diuretic and Natriuretic Properties", by T. G. Flynn, et al.
Jan. 6, 1984, Science Volume, pp. 67–69, "Purification and Sequence Analysis of Bioactive Atrial Peptides (Atriopeptins)", by Mark G. Currie, et al.
Biochem. and Biophys. Res. Commun., vol. 118, No. 1, 1984, pp. 131–139, "Purification and Complete Amino Acid Sequence of Human Atrial Natriuretic Polypeptide (HANP)", by Kenju Kangawa, et al.
Biochem. and Biophys. Res. Commun., vol. 119, No. 2, 1984, pp. 524–529, "Rat Atrial Natriuretic Factor: Complete Amino Acid Sequence and Disulfide Linkage Essential for Biological Activity", by K. S. Misono, et al.
Kangawa, K. et al., Biochem. Biophys. Res. Commun., 119 (3):933–940 (1984).
Garcia, R. et al., Biochem. Biophys. Res. Commun., 126 (1):178–184 (1985).
Katsube, N. et al., Biochem. Biophys. Res. Commun., 128 (1):325–330 (1985).
"Relationship of Specific Granules to the Natriuretic and Diuretic Activity of Rat Atria", by R. Garcia, et al., Jan. 1982, Experientia, 38:1071–73.

Primary Examiner—Delbert R. Phillips
Attorney, Agent, or Firm—Limbach, Limbach & Sutton

[57] ABSTRACT

Methods and compositions are provided for inducing natriuresis, diuresis and vasodilatation in mammalian hosts by administering auriculin or a synthetic analog of auriculin to said host.

10 Claims, 7 Drawing Figures

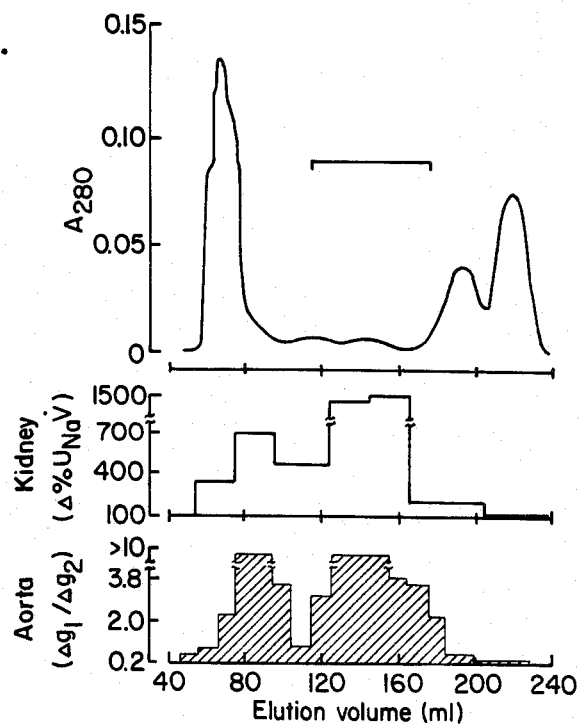
FIG._1A.
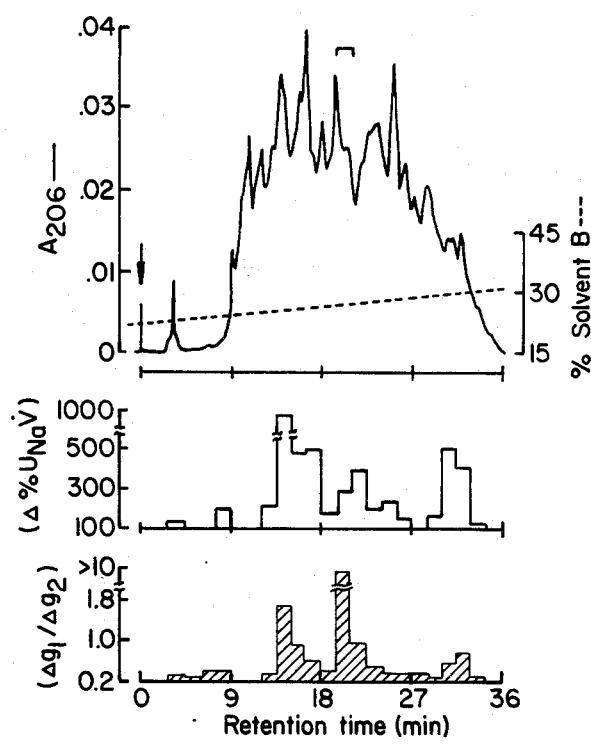
FIG._1B.

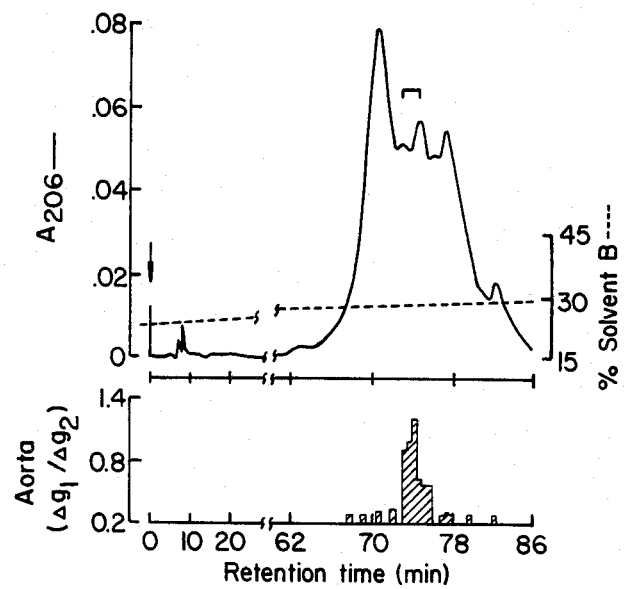
FIG._1C.
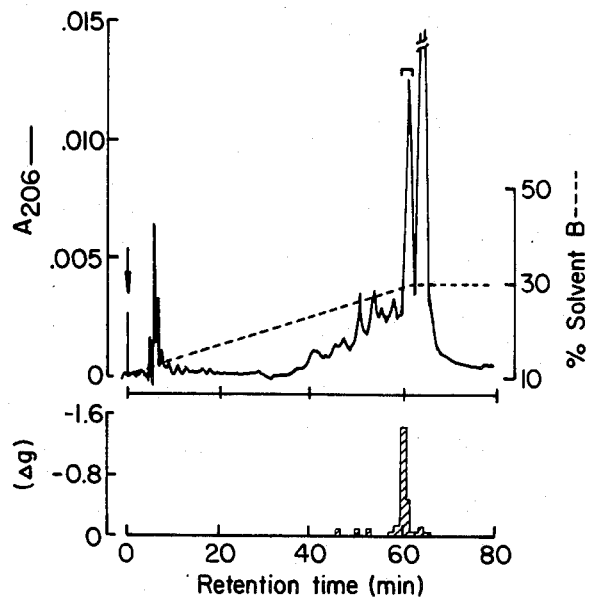
FIG._1D.

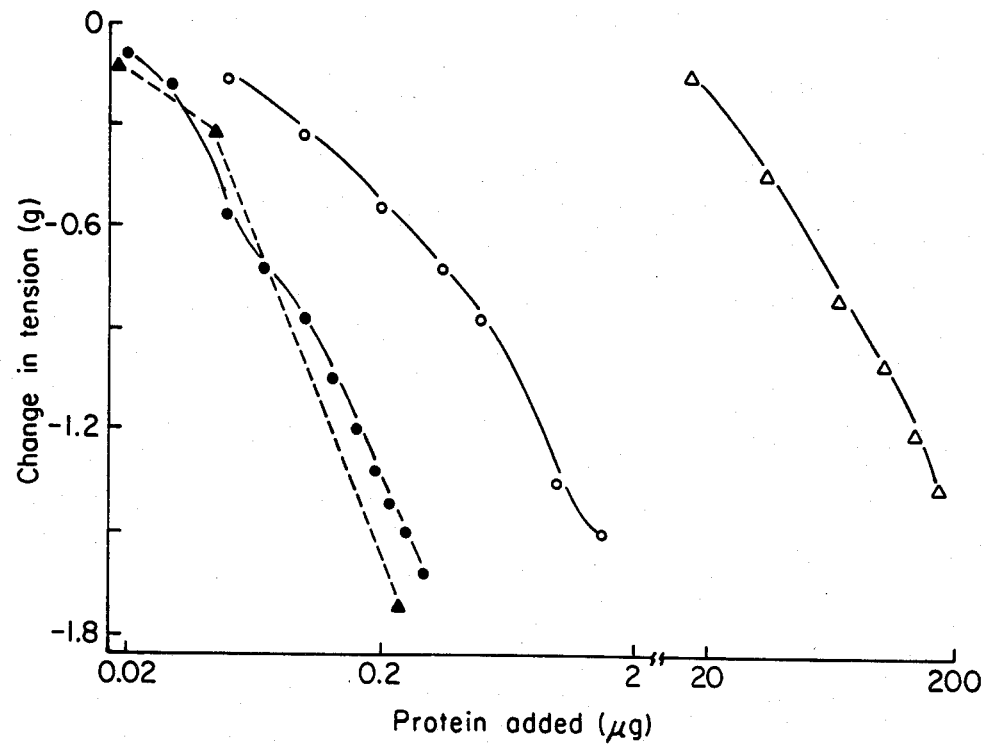
FIG._2.
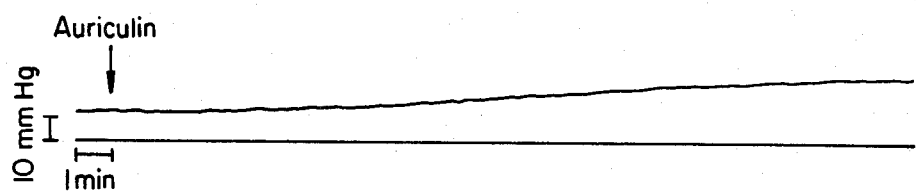
FIG._3A.
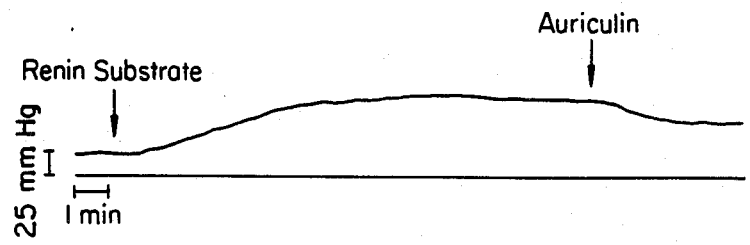
FIG._3B.

NOVEL POLYPEPTIDE DIURETIC/VASODILATORS

TECHNICAL FIELD

The present invention relates generally to polypeptides capable of regulating sodium excretion and blood pressure in mammals. More particularly, the present invention is directed to methods and compositions analogous to polypeptides isolated from atrial tissue which are capable of inducing diuresis, natriuresis and vasodilatation by the pharmaceutical administration of effective amounts of selected polypeptides.

BACKGROUND ART

Most multi-cellular organisms are organized into tissues and organs which perform specialized functions. Thus, a system has evolved to transport materials between them. In higher animals, including mammals, this circulatory system is closed to improve the efficiency of transport. The flow of blood fluid through this closed cardiovascular system requires that the fluid be maintained under pressure and the regulation of the systemic arterial blood pressure requires a complex interaction of numerous factors including, e.g., fluid volume and vascular elasticity and caliber.

The maintenance of normal extracellular fluid volume depends primarily on the excretion of sodium (natriuresis) and water (diuresis) by the kidneys. This is determined by (1) the rate at which plasma is filtered at the glomerulus (glomerular filtration rate, or GFR) and (2) the degree to which sodium is actively reabsorbed along the renal tubule (with water following passively). The latter process is in part regulated by the adrenal steroid hormone aldosterone. It has been long believed that, in addition to GFR and aldosterone, there must be a "third factor" which also regulates sodium reabsorption. It is now apparent that many of the phenomena which required the postulation of a "third factor" can be explained by the effects of physical forces (e.g. blood pressure, red blood cell concentation and plasma viscosity) on sodium reabsorption. Nonetheless, the search continues for a "natriuretic hormone" which might directly inhibit tubular reabsorption.

There are several candidates for such a hormone, among which are included the natriuretic factor(s) recently isolated from atrial muscle cells. A natriuretic effect has been demonstrated by crude extracts of rat atrial tissue but not ventricular tissue. De Bold, A.J. et al., Life Sciences, 28:89–94 (1981), Garcia, R., Experientia, 38:1071–73 (1982), Currie, M.G. et al., Science 221:71–73 (1983). Various peptides with diuretic and natriuretic properties have been isolated from atrial tissue and sequenced. Flynn, T.G. et al., Biochem. Biophys. Res. Commun. 117:859–865 (1983), Currie, M.G. et al., Science 223:67–69 (1984), Kangawa, K. et al., Biochem. Biophys. Res. Commun. 118:131–139 (1984). The existence of these atrial natriuretic factors strengthens the long-held suspicion that the heart, aside from its obvious influence on renal perfusion, may play an important role in regulating renal sodium and water excretion. Stretching of the atria is known to induce diuresis and natriuresis, and this is possibly mediated by increased release of these factors.

A number of clinically important disease states are characterized by abnormal fluid volume retention. Congestive heart failure, cirrhosis of the liver and the nephrotic syndrome each lead to excessive fluid accumulation on the venous side of the circulation, the presumed common mechanism being under-perfusion of the kidneys leading to a fall in GFR. In addition the reduced renal perfusion stimulates excessive secretion of renin, a proteolytic enzyme whose action in the circulation leads to the formation of angiotensin. Angiotensin is a powerful constrictor of arterioles (which helps to maintain arterial pressure) and also stimulates release of the sodium-retaining hormone aldosterone by the adrenal gland (which further worsens fluid retention). These mechanisms do not, however, fully account for the fluid retention of the so-called "edematous states", and additional factors are likely to be involved. One important possibility is that a relative or absolute deficiency of atrial natriuretic factor, caused either by chronic over-stretching of the atrium (e.g., heart failure) or by inadequate stimulation of the atrium (e.g., cirrhosis and nephrotic syndrome), might contribute to the fluid retention.

An increase in extracellular fluid volume is also thought to contribute to the development of hypertension in many instances. Hypertension, or chronically elevated blood pressure, is one of the major causes of illness and death worldwide. It is estimated that more than 20 million Americans suffer from this disease whose complications include heart failure, heart attack, stroke and kidney failure. The major observed hemodynamic abnormality in chronic hypertension is increased resistance to the flow of blood through the arterioles. The mechanisms which lead to this increased "peripheral resistance" are, however, incompletely understood. In some cases inappropriate activity of the renin-angiotensin system or sympathetic nervous system may lead to excessive constriction of the arterioles; by "inappropriate" it is meant that the unknown signal(s) leading to this activity are not based upon a physiological need of the organism and thus lead to elevated blood pressure (whereas, in the example cited earlier, the increased renin secretion in the edematous states is a response to reduced arterial pressure and thus helps to restore or maintain normal pressure). In a substantial fraction of hypertensives however, inappropriate sodium and volume retention by the kidney is felt to either initiate or contribute to the elevated blood pressure. The responsible defect in kidney function and the mechanism whereby fluid retention leads to increased peripheral resistance are both unknown. It is certainly possible that deficiency of a natriuretic hormone could be responsible for these observations, particularly if the same substance also normally exerted a relaxant effect on arterioles.

Diuretic therapy is currently a mainstay in the treatment of hypertension, renal failure and the various edematous states (heart failure, etc.). Currently available pharmacological preparations have, however, several important limitations and undesirable effects. While their use may be directed at a specific abnormality (i.e. volume expansion), their multiple actions are undoubtedly not physiological, leading for instance to potassium depletion, increased retention of uric acid and abnormal glucose and lipid metabolism. In addition, all known diuretics profoundly stimulate the renin-angiotensin-aldosterone system, which counteracts their volume-depleting and blood pressure-lowering effects and leads to other unwanted effects. It would be desirable to provide a pharmacologically effective compound which can regulate blood pressure by providing a complete but controlled range of physiological responses.

Accordingly, it is the principal object of the present invention to provide methods and compounds for influencing fluid volume and blood pressure homeostasis in mammals.

It is another object of the present invention to provide methods and compounds which mimic the physiological regulation of fluid volume and blood pressure in mammals.

DISCLOSURE OF THE INVENTION

The obtainment of these and other objects of the invention is provided by methods and compositions of the present invention which include auriculin substantially free of unrelated atrial tissue or products.

Compositions of the present invention useful as natriuretics, diuretics, vasodilators and modulators of the renin-angiotensin-aldosterone system include polypeptide compounds identified by the formula:

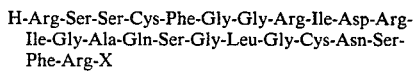

where X is OH or Tyr-OH

Also provided are methods for using compounds of the present invention as diagnostic and therapeutic agents.

BRIEF DESCRIPTION OF THE DRAWINGS

FIG. 1A–D are graphic representations of the purification of compounds of the present invention from atrial tissue, in which:

FIG. 1A displays the results of G-50 gel filtration of crude extract;

FIG. 1B displays the results of HPLC ($C_{18}$ column) purification of refined extract;

FIG. 1C displays the re-chromatography of the product of FIG. 1B; and

FIG. 1D displays the results of HPLC (CN column) purification of the purified active fractions of FIG. 1C;

FIG. 2 is a comparison of the vasorelaxant activity of purified and synthetic compounds of the present invention; and FIG. 3 is a comparison of the vascular action of synthetic compounds of the present invention in the absence (A) or presence (B) of angiotensinogen (the precursor cleaved by renin to produce angiotensin).

BEST MODE FOR PRACTICING THE INVENTION

In accordance with the present invention methods and compositions are provided for the regulation of fluid volume and blood pressure in mammals, in which one aspect of the invention provides auriculin substantially free of unrelated atrial tissue or products.

Another aspect of the invention provides polypeptide compounds comprising the formula:

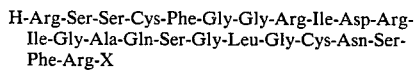

where X is OH or Tyr-OH

The nomenclature used to describe polypeptides of the present invention follows the conventional practice of using the first three letters of the trivial name of the amino acid and wherein the L form of any amino acid having an optical isomer is intended unless otherwise expressly indicated.

Compounds within the scope of the present invention can also be obtained by modifying the above recited formula in numerous ways while preserving the activity of the polypeptides thus obtained. For example, while the amino acids of these polypeptide compounds are normally in the natural L form, one or more, usually two or less and preferably one amino acid may be replaced with the optical isomer D form. Amino acid residues contained within the polypeptide compounds can also be modified by acetylation or substituted with other chemical groups which can, for example, change the solubility of the compounds without effecting their activity.

In addition, one or more amino acid residues can be replaced by functionally equivalent residues; for example basic amino acids can be replaced with other basic amino acids and acidic amino acids can be replaced with other acidic amino acids. However, the replacement of hydrophobic amino acids, particularly cysteine, are considered less desirable due to the likelihood of interfering with the presumptive disulfide bridge between residues 4 and 20.

Further modifications are possible by extending or decreasing, preferably extending, the compounds' amino acid sequence by the addition of amino acids or oligopeptides on the N-terminal or preferably C-terminal end of the sequence disclosed above. Particularly, X can be amide or an amino acid or oligopeptide of not more than about 8, usually 5, and desirably 4 amino acids which do not adversely effect natriuretic, diuretic and vasorelaxant activity of the subject compounds. Furthermore, compounds of the present invention can be bonded to or conjugated with compounds having the same range of activities to obtain the benefits of the present invention.

Preferred compounds of the present invention have been isolated from atrial tissue of rats, substantially free of unrelated atrial tissue or products. Generally, acetic acid extracts of atrial tissue are subjected to gel filtration, and reversed phase high performance liquid chromatography (using $C_{18}$ and CN columns), while assaying for the natriuretic and vasorelaxant activity of the fractions.

Compounds within the scope of the present invention can be isolated and purified from biological tissue sources, notably mammalian atrial tissue sources, or can be synthesized chemically by means well-known in the art such as, e.g., solid phase synthesis. The synthesis is commenced from the C-terminal end of the peptide using an alpha-amino protected amino acid. t-Butyloxycarbonyl (Boc) protective groups can be used for all amino groups even though other protective groups are suitable. For example, Boc-Arg-OH or Boc-Tyr-OH (i.e., the C-terminal amino acids) can be esterified to brominated polystyrene resin supports. The polystyrene resin support is preferably a copolymer of styrene with about 0.5 to 2% divinyl benzene as a cross-linking agent which causes the polystyrene polymer to be completely insoluble in certain organic solvents. See Stewart et al., Solid-Phase Peptide Synthesis, W. H. Freeman Co., San Francisco (1969) and Merrifield, J., Am. Chem. Soc. 85:2149–2154 (1963).

Conveniently, polypeptides may be synthesized automatically employing, for example, a Biosearch SAM II automatic peptide synthesizer (Biosearch, Inc. San Rafael, California) as described in the instruction manual.

Compounds of the present invention are shown to have natriuretic and diuretic activity in the intact mammal and in the kidney isolated from a mammal. Furthermore, compounds of the present invention including synthetic compounds, possess vasorelaxant activity, which has been shown to be enhanced by slow oxidation, which indicates the likelihood of a disulfide Cys-Cys bridge between residues 4 and 20 in the general formula indicated previously.

Compounds of the present invention which are shown to have the above recited physiological effects can find use in numerous therapeutical applications such as, e.g., inducing natriuresis, diuresis, and vasodilatation. Thus these compounds can find use as therapeutic agents in the treatment of various edematous states such as, for example, congestive heart failure, nephrotic syndrome and hepatic cirrhosis, in addition to hypertension and renal failure due to ineffective renal perfusion or reduced glomerular filtration rate.

These compounds can be administered to mammals for veterinary use such as with domestic animals, and clinical use in humans in a manner similar to other therapeutic agents, that is in a physiologically acceptable carrier. In general the dosage will range from about 0.01 to 100 µg/kg, more usually 0.1 to 10 µg/kg of the host body weight. Alternatively, dosages within these ranges can be administered by constant infusion over an extended period of time, usually exceeding 24 hours, until the desired therapeutic benefits have been obtained.

These compounds can be administered neat, as mixtures with other physiologically acceptable active or inactive materials, or with physiologically suitable carriers such as, for example, water or normal saline. The compounds can be administered orally or parenterally, for example, by injection. Injection can be subcutaneous, intravenous, or by intramuscular injection.

These compounds are desirably administered in pharmaceutically effective amounts and often as pharmacologically acceptable salts such as acid addition salts. Such salts can include, e.g., hydrochloride, hydrobromide, phosphate, sulphate, acetate, benzoate, malate, among others.

Compounds of the present invention can also be used for preparing antisera for use in immunoassays employing labelled reagents, usually antibodies. Conveniently, the polypeptides can be conjugated to an antigen by means of dialdehydes, particularly from 4 to 6 carbon atoms and aliphatic, or carbodiimide. These compounds and immunologic reagents may be labelled with a variety of labels such as chromophores, fluorophores such as, e.g., fluorescein or rhodamine, radioisotopes such as $^{125}I$, $^{35}S$, $^{14}C$, or $^{3}H$, or magnetized particles, by means well known in the art.

These labeled compounds and reagents, or labeled reagents capable of recognizing and specifically binding to them, can find use as, e.g., diagnostic reagents. Samples derived from biological specimens can be assayed for the presence or amount of substances having a common antigenic determinant with compounds of the present invention. In addition, monoclonal antibodies can be prepared by methods known in the art, which antibodies can find therapeutic use, e.g., to neutralize overproduction of immunologically related compounds in vivo.

The following examples are provided by way of illustration, rather than implying any limitation of the subject invention.

EXPERIMENTAL

Isolation and Purification

The following compound was isolated from atrial tissue as follows:

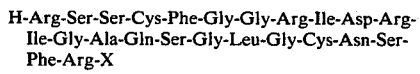

H-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-X where X is OH or Tyr-OH These compounds and their synthetic polypeptide analogs are referred to as auriculin.

The polypeptide was purified from an acetic acid extract of atria from 1400 male Wistar rats by first homogenizing the tissue in 8 volumes of 1 N acetic acid containing 1 mM phenylmethylsulfonyl fluoride (PMSF Sigma Chemical Co., St. Louis, Mo.), 3 mM ethylenediaminetetraacetic acid (EDTA) and 5 µM pepstatin A (pepsin and renin inhibitor, Sigma Chemical Co., St. Louis, MO). This homogenate was centrifuged at 10,800×g for 30 minutes and the pellet was rehomogenized in 4 volumes of the original buffer. The supernate from the second extract was pooled and the pooled supernatants were neutralized with ammonium hydroxide. The neutralized supernatants were then centrifuged at 10,000×g for 20 minutes and lyophilized.

The lyophilized extract was subjected to gel filtration on a 2.5×45 cm column of Sephadex ® G-50 (fine, Pharmacia Fine Chemicals, Piscataway, NJ) which had been equilibrated with 1 N acetic acid. The lyophilized extract was reconstituted with 6 ml buffer, centrifuged and applied to the column and then eluted at a flow rate of 0.63 ml/minute. Aliquots from each fraction were dried (Savant Speed-Vac concentrator), reconstituted in phosphate buffered saline (PBS) and assayed for natriuretic activity in intact rat and for vasorelaxant activity using rabbit aortic rings.

The results of this chromatographic step were as shown in FIG. 1A, and the regions contained in horizontal bracket were lyophilized, reconstituted with 0.1% aqueous trifluoroacetic acid (TFA), pooled and centrifuged.

The pooled material was adjusted to 15% acetonitrile ($CH_3CN$) and was applied to a 0.39×30.0 centimeter µ-Bondapak $C_{18}$ column (Waters, Inc., Milford, MA). The material was applied using a Waters U6K injector and solvent delivery system (Waters, Inc., Milford, MA). Bound material was eluted at 0.1 ml/min. with a linear gradient of solvents A (0.1% TFA): B ($CH_3CN$) from 85:15 to 45:55 over 40 minutes.

Aliquots of the fractions were assayed for natriuresis in the isolated kidney and vasorelaxant activity as described subsequently. A broad region of coincident natriuretic and vasorelaxant activity was eluted and these fractions were pooled and dried.

The material obtained and dried was reconstituted in A:B, 78:22, and rechromatographed (in 12 separate applications) at 1.0 ml/min. using a gradient of 22 to 34% B over 48 minutes. Aliquots of the fractions were tested for natriuretic and vasorelaxant activities as described above. The results were as displayed in FIG. 1B. Fractions from the three active peaks were pooled and dried overnight.

The combined fractions from the second peak (indicated by bracketed area in FIG. 1B) was reconstituted in A:B, 77:23, applied to a $C_{18}$ column and eluted at 0.4 ml/min. using a gradient of 23 to 29% B over 90 minutes. The results of this rechromatography were as shown in FIG. 1C, where the bracketed area indicates fractions with vasorelaxant activity. Active fractions from 6 applications were pooled.

The material thus obtained was applied to a 0.39×30 cm μ-Bondapak CN column (Waters, Inc., Milford, MA). The solvent system used was A (0.1% TFA in water) and B (0.055% TFA in $CH_3CN$). The sample was reconstituted in A:B, 90:10, and chromatographed in three separate applications at 0.6 ml/min. using a gradient of 10 to 30% B over 60 minutes. Vasorelaxant activity was determined by the reduction in tension produced in histamine-contracted aortic rings as described subsequently.

The active peak, indicated by the bracket in FIG. 1D, was dried and sequenced. The sequence was determined from one nanomole of protein using the Applied Biosystems 470A gas-phase sequencer (Applied Biosystems Inc., Foster City, CA) in accordance with the instructions of the manufacturer. PTH amino acids were identified with a Beckman 334 T HPLC, using a 0.46×25 cm IBM CN-column. The gradient applied was as indicated in Hunkapiller, N. W. and L. E. Hood, *Methods in Enzymology*, 91:486–492 (Academic Press, New York) (1983), with the following modifications:the binary gradient system of Hunkapiller and Hood has been replaced by a ternary gradient system in which acetonitrile and methanol are pumped by separate pumps and the ratio of the two varied with time over the course of the gradient, with appropriate modification of the gradient program; the Permaphase ETH ® guard column, specified by Hunkapiller and Hood, has been replaced with a 5×0.46 centimeter IBM CN analytical "minicolumn"; and the analytical column is heated to 28° C whereas Hunkapillar and Hood specify 32° C.

Because of the methods used to assay the products of the purification procedure, natriuretic and vasorelaxant activity is an inherent property of the isolated and purified material.

Chemical Synthesis

Compounds of the present invention having the formula:

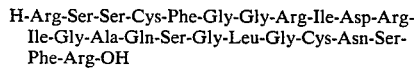

H-Arg-Ser-Ser-Cys-Phe-Gly-Gly-Arg-Ile-Asp-Arg-
Ile-Gly-Ala-Gln-Ser-Gly-Leu-Gly-Cys-Asn-Ser-
Phe-Arg-OH were synthesized by solid-phase techniques. Synthesis was performed on a Biosearch SAM II automated peptide synthesizer using t-BOC amino acids in accordance with the instructions of the manufacturer.

Following repetitive deblocking cycles with TFA, subsequent couplings of amino acids were achieved with a water-soluble carbodiimide. Synthetic peptide was removed from the polystyrene resins with liquid HF, then was reduced, purified and slowly reoxidized in accordance with the protocol of Rivier, J. E. F., J. Amer. Chem. Soc., 96:2986–2992 (1974).

The polypeptide material was dissolved in 1 N acetic acid containing 10 mM β-mercaptoethanol and applied to a 2×96 cm column of Sephadex ® G-25 (Pharmacia Fine Chemicals) equilibrated with the same buffer. The flow rate used was 0.335 ml/min. The major peak of UV (250 nm) absorbing material was lyophilized, resuspended in 0.05 M ammonium acetate, pH 7.2, to a final concentration of 50 μg/ml. This material was allowed to reoxidize by exposure to air at 4° C. in the dark for 60 hours and then lyophilized.

This polypeptide material was compared to partially-purified (FIG. 1A) and purified (FIG. 1D) auriculin for its ability to relax histamine-contracted aortic rings. Aortic ringswere suspended in 10 ml aerated Kreb's buffer under 1.5 grams passive tension. The rings were precontracted with $6 \times 10^{-6}$ M norepinephrine, washed and allowed to return to baseline tension. A sustained contraction was induced with 5 μM histamine and increasing amounts of purified or synthetic peptide were added in cumulative fashion. The change in tension is related to the cumulative amount of protein added, as shown in FIG. 2, wherein the open triangles represent polypeptide purified by gel filtration only, closed triangles represent completely purified polypeptide, open circles represent synthetic peptide before oxidation and closed circles represent synthetic polypeptide after oxidation.

Biologic Activity

The biologic activities of auriculin and its chemically synthesized analog were determined and compared using intact rats, isolated rat kidneys, intact dogs and isolated rabbit thoracic aortic rings.

The synthetic auriculin analog was compared to partially purified (gel filtration step) and purified (HPLC) auriculin for its ability to relax histamine-contracted aortic rings. Rings were suspended in 10 ml aerated Kreb's buffer under 1.5 g passive tension. Rings were precontracted with $6 \times 10^{-6}$ M norepinephrine, washed and allowed to return to baseline tension, as described (Kleinert, H. D. (1984), supra). A sustained contraction was induced with 5 uM histamine and then increasing amounts of purified auriculin or synthetic polypeptide were then added in cumulative fashion. The change in tension was shown to be related to the cumulative amount of protein added, as seen in FIG. 2.

As alternatives, angiotensin, norepinephrine and potassium-induced depolarization were used instead of histamine. Purified and synthetic auriculin demonstrated similar vasorelaxant effects.

The synthetic polypeptide auriculin analog was also found to be natriuretic in the intact rat. Synthetic peptide was administered as a bolus injection to Inactin anesthetized rats (100 mg/kg, average weight 399 g) which were maintained on a constant infusion of normal saline at 2.2 ml/hr. The results were as shown in Table I, wherein the change in each parameter was assessed by the difference between the average of three control periods (10 mins. each) and the first experimental period (maximum response). Data are expressed as mean ±SE.

TABLE I

| | Natriuretic Effect of Synthetic Auriculin in Intact Rats | | |
|---|---|---|---|
| Dose (μg/kg) | V̇ (μl/min) | $U_{Na}\dot{V}$ (μEq/min) | $U_K\dot{V}$ (μEq/min) |
| 1.2 (n = 4) | 25.5 ± 9.7 | 2.5 ± 1.1 | 1.6 ± 0.2 |
| 2.6 (n = 4) | 41.3 ± 19.5 | 6.7 ± 4.1 | 4.4 ± 1.4 |
| 5.0 (n = 4) | 52.8 ± 6.5 | 9.1 ± 1.0 | 3.7 ± 0.5 |
| 7.2 (n = 3) | 112.0 ± 12.8 | 18.3 ± 0.5 | 3.1 ± 0.8 |

V̇, urine flow rate; $U_{Na}\dot{V}$, urinary sodium excretion rate; $U_K\dot{V}$, urinary potassium excretion rate. Control values for the 15 animals were: V̇, 1 0.3 ± 2.9 μl/min; $U_{Na}\dot{V}$, 0.93 ± 0.5 μEq/min; and $U_K\dot{V}$, 1.6 ± Eq/min.

The natriuretic activity of the synthetic polypeptide auriculin analog was also measured in isolated rat kidney. Functioning isolated rat kidneys were perfused in a closed-circuit system, as described in Camargo, M.J.F. et al. Am.J.Physiol., In Press. (1984). After control clearance periods, 150 ng of synthetic peptide was added to the perfusate. The effects on each parameter were noted immediately and reached a maximum during the fourth 10 minute clearance period. These peak values are expressed in Table II as the experimental data.

TABLE II

Effects of Synthetic Auriculin on Renal Function in the Isolated Perfused Rat Kidney

| | Control | Experimental |
|---|---|---|
| GFR (ml/min) | 0.43 ± 0.05 | 0.63 ± 0.03* |
| FF | 0.014 ± 0.002 | 0.021 ± 0.001* |
| RVR (mmHg/ml · min) | 2.9 ± 0.1 | 3.9 ± 0.3* |
| V̇ (μl/min) | 19.8 ± 4.8 | 97.6 ± 19.4* |
| $FL_{Na}$ (μEq/min) | 60.2 ± 7.9 | 90.1 ± 5.2* |
| $T_{Na}$ (μEq/min) | 60.0 ± 7.6 | 84.2 ± 4.8* |
| $U_{Na}\dot{V}$ (μEq/min) | 0.66 ± 0.35 | 6.01 ± 1.99* |
| $FE_{Na}$ (%) | 0.97 ± 0.38 | 6.6 ± 2.0* |
| $U_K\dot{V}$ (μEq/min) | 0.44 ± 0.19 | 1.46 ± 0.16* |
| $FE_K$ (%) | 19.8 ± 5.9 | 52.1 ± 6.2* |

GFR, glomerular filtration rate; FF, filtration fraction; RVR, renal vascular resistance; V̇, urine flow rate; $FL_{Na}$, filtered load of sodium; $T_{Na}$, tublular reabsorption of sodium; $U_{Na}\dot{V}$, urinary sodium excretion rate; $FE_{Na}$, fractional sodium excretion; $U_K\dot{V}$, urinary potassium excretion rate; $FE_K$, fractional potassium excretion. Results are the mean ± SE of 4 kidneys.
*P 0.05 compared to control (Student's t test).

In these results it can be seen that isolated kidneys perfused in the absence of vasoconstrictors, the synthetic polypeptide increased renal vascular resistance (see also FIG. 3A), filtration fraction and glomerular filtration rate. In contrast, in isolated kidney pre-contracted with endogenously agnerated angiotensin, the synthetic peptide decreased vascular resistance (see FIG. 3B). These effects with the synthetic peptide show that auriculin can have both renal vasoconstrictive and vasorelaxant activity depending on the absence or presence of endogenous vasoconstrictors. The natriuresis observed in the isolated kidney can result from a renal vasoconstrictive effect preferentially expressed in the efferent arteriole.

Renal and hemodynamic effects have also been measured in anesthetized dogs receiving a constant infusion of the synthetic peptide (1 μg/kg bolus, followed by 0.1 μg/kg/min for 1 hour). Immediate effects were noted on blood pressure, GFR and urine flow rate and electrolyte excretion which were sustained throughout the infusion. The "experimental" data presented for these parameters in Table III are the average values obtained during the infusion. Mean arterial pressure (MAP) fell consistently by 10-15% while GFR rose by 25-35%, in association with a sustained diuresis and natriuresis (Table III). All these parameters returned to control (i.e. pre-infusion) levels during the recovery period (i.e. following termination of the infusion).

TABLE III

Hemodynamic, Renal and Metabolic Effects Of Synethetic Auriculin in Anesthetized Dogs

| | Control | Experimental | Recovery |
|---|---|---|---|
| MAP (mm Hg) | 134 ± 5 | 122 ± 4*+ | 136 ± 4 |
| GFR (ml/min) | 25.5 ± 2.7 | 32.3 ± 4.1*+ | 25.4 ± 3.3 |
| V̇ (ml/min) | 0.21 ± 0.03 | 1.06 ± 0.14*+ | 0.37 ± 0.05 |
| $FE_{H_2O}$ (%) | 0.9 ± 0.2 | 3.4 ± 0.3*+ | 1.5 ± 0.2 |
| $U_{Na}\dot{V}$ (Eq/min) | 38 ± 6 | 187 ± 35*+ | 68 ± 14 |
| $FE_{Na}$ (%) | 1.1 ± 0.2 | 4.1 ± 0.5*+ | 1.9 ± 0.4 |
| $U_K\dot{V}$ (Eq/min) | 15 ± 2 | 36 ± 6*+ | 21 ± 4 |
| $FE_K$ (%) | 18 ± 1 | 34 ± 6*+ | 21 ± 4 |
| PRA (ng/ml/hr) | 13 ± 2.0 | 8.3 ± 1.8*+ | 14 ± 2.5 |

TABLE III-continued

Hemodynamic, Renal and Metabolic Effects Of Synethetic Auriculin in Anesthetized Dogs

| | Control | Experimental | Recovery |
|---|---|---|---|
| PA (ng/100 ml) | 8.5 ± 1.9 | 5.4 ± 0.9* | 7.0 ± 1.3 |

MAP, mean arterial pressure (blood pressure); $FE_{H_2O}$, fractional water excretion; PRA, plasma renin activity; PA, plasma aldosterone. For definition of other abbreviations see footnote to Table II. *P<0.05 compared to control; +P<0.05 compared to recovery.

The peptide produced significant decreases in plasma renin activity (PRA) and plasma aldosterone (PA), as shown in Table III. Additional studies demonstrate that this substance also inhibits the ability of angiotensin to stimulate aldosterone production by isolate adrenal cells. Thus, auriculin is potentially able to block the effects of the reninangiotensin system at several levels including: (1) it antagonizes the direct actions of angiotensin on its target organs (blood vessels and the adrenal); and (2) it inhibits renin sectretion, which leads to a reduced rate of angiotensin formation in the blood.

Based on the above data, it is evident that the synthetic and tissue derived auriculin polypeptides possess similar activity, desirably after the synthetic auriculin polypeptide has been allowed to oxidize promoting the formation of disulfide bridges.

It is also evident from the above results that the subject compounds can be used as a potent vasorelaxant, diuretic and natriuretic in mammalian hosts.

Production of Antibody to Auriculin

Compounds of the present invention were used to provide immunoassays, particularly radioimmunoassays, for the determination of the presence or amount of auriculin in samples.

Antibody to auriculin was produced by immunizing New Zealand white rabbits subcutaneously and intramuscularly with 250 μg auriculin conjugated to bovine serum albumin in complete Freund's adjuvant. Rabbits were boosted at three week intervals with an identical quantity of conjugate in incomplete Freund's adjuvant. The rabbits were bled from the ear artery 7-10 days after a boost and the resulting serum was tested for its ability to bind auriculin. Parallel control nonimmune serum samples were also tested. Table IV presents data from a representative experiment in which the ability of antisera to interact specifically with auriculin was examined. Auriculin (500 nanograms) was immobilized at individual wells of a polystyrene plate. Varying dilutions of antisera were then added to these wells and the amount of antibodies specifically bound was quantified by adding $^{125}$I-labeled sheep anti-rabbit IgG antisera. This is a standard method for determining specific antibody titres. As shown in Table IV, at a serum dilution of 1:400 significant quantities of antibody were still binding to auriculin. Specific binding was not observed with non-immune serum.

TABLE IV

Specific Binding of Anti-Auriculin Antisera to Immobilized Auriculin

| | Antibody Bound (CPM) | |
|---|---|---|
| Antiserum Dilution | Immune | Non-Immune |
| 1:10 | 7481 | 734 |
| 1:50 | 6977 | 681 |
| 1:100 | 6135 | 685 |
| 1:200 | 5096 | 634 |
| 1:400 | 3898 | 525 |

The experiment depicted in Table V is identical to that of Table IV, however, varying concentrations of non-immobilized auriculin were added concurrently with a 1:100 dilution of anti-auriculin antiserum. As shown, non-immobilized auriculin competitively displaced antibody binding from immobilized auriculin. Thus, this serves as an example of a competitive displacement assay. This assay, or similar radioimmunoassays, can be used to quantify auriculin-like immunoreactivity in tissues or serum under a variety of physiological or pathophysiological states. Thus far, the assay has been used to detect auriculin in atrial extracts. Auriculin was not detected in ventricular extracts.

TABLE V

Competitive Displacement of Anti-Auriculin Binding To Immobilized Auriculin by Addition of Free Auriculin

| Conc. Free Auriculin (nmoles) | Antibody Bound (CPM) |
| --- | --- |
| 0 | 6777 |
| 0.002 | 6343 |
| 0.02 | 5603 |
| 0.2 | 2893 |
| 2.0 | 1223 |

Although the foregoing invention has been described in some detail by way of clarity and for purposes of understanding, it will be understood by those skilled in the art that modifications of the invention may be practiced while remaining within the spirit and scope of the appended claims.

We claim:

1. A polypeptide compound useful as a natriuretic, diuretic and vasorelaxant in mammals, said polypeptide compound comprising the formula:

H-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-X where X is OH or Tyr-OH; and including such compound containing a disulfide bridge joining the cysteine residues, and the pharmacologically acceptable salts thereof.

2. Antisera and antibodies which are capable of recognizing and specifically binding to immunoreactive polypeptides comprising the polypeptides of claim 1.

3. A pharmaceutical composition useful as a natriuretic, diuretic and vasorelaxant in mammals, comprising a polypeptide compound in accordance with claim 1 in a therapeutically effective amount, together with a physiologically suitable carrier.

4. A method for inducing natriuresis and diuresis in a mammalian host which comprises administering to said host a pharmaceutically effective amount of the polypeptides of claim 1 or 3.

5. A method for inducing vasodilatation and blood pressure reduction in a mammalian host which comprises administering to said host a pharmaceutically effective amount of the polypeptides of claim 2 or 3.

6. A method for modulating angiotensin-induced aldosterone release in a mammalian host in need of said modulation which comprises administering to said host a pharmaceutically effective amount of the polypeptides of claim 2 or 3.

7. A method for inhibiting renin secretion in a mammalian host in need of said inhibition which comprises administering to said host a pharmaceutically effective amount of the polypeptides of claim 2 or 3.

8. A method for the treatment of congestive heart failure, nephrotic syndrome, hepatic cirrhosis and other conditions characterized by chronic increased extracellular fluid volume and ineffective renal perfusion, in a mammalian host in need of said treatment which comprises administering to said host a pharmaceutically effective amount of the polypeptides of claim 1 or 3.

9. A method for the treatment of hypertension in a mammalian host in need of said treatment which comprises administering to said host a pharmaceutically effective amount of the polypeptides of claim 2 or 3.

10. A method for the treatment of renal failure which is characterized by ineffective renal perfusion or reduced glomerular filtration rate in a mammalian host in need of said treatment which comprises administering to said host a pharmaceutically effective amount of the polypeptides of claim 2 or 3.

* * * * *

UNITED STATES PATENT AND TRADEMARK OFFICE
CERTIFICATE OF CORRECTION

PATENT NO. : 4,618,600
DATED : Oct. 21, 1986
INVENTOR(S) : Johnson et al.

It is certified that error appears in the above—identified patent and that said Letters Patent is hereby corrected as shown below:

Col. 7, line 29 "modifications:the" should be --modifications: the--

Col. 8, line 7 "ringswere" should be --rings were--.

Col. 9, line 34 "agnerated" should be --generated--.

Col. 10, line 7 "$FE_{H2}O$" should be --$FE_{H_2O}$--.

Col. 10, line 20 "sectretion" should be --secretion--.

Signed and Sealed this

Twenty-first Day of April, 1987

*Attest:*

DONALD J. QUIGG

*Attesting Officer*  *Commissioner of Patents and Trademarks*